United States Patent [19]
Ray et al.

[11] Patent Number: 6,109,895
[45] Date of Patent: Aug. 29, 2000

[54] PORTABLE PERISTALTIC PUMP

[75] Inventors: Claude Ray, Montezillon, Switzerland; Christian Taillard, Les Fins, France

[73] Assignee: Conseil-Ray S.A., La Chaux-de-Fonds, Switzerland

[21] Appl. No.: 09/254,581

[22] PCT Filed: Sep. 8, 1997

[86] PCT No.: PCT/CH97/00327

§ 371 Date: Mar. 8, 1999

§ 102(e) Date: Mar. 8, 1999

[87] PCT Pub. No.: WO98/11349

PCT Pub. Date: Mar. 19, 1998

[30] Foreign Application Priority Data

Sep. 10, 1996 [FR] France ................................. 96 11170

[51] Int. Cl.[7] .................................................. F04B 43/08
[52] U.S. Cl. ...................... 417/477.2; 417/477; 417/374
[58] Field of Search .................................. 417/477, 234, 417/374, 474, 477.2; 210/646, 85; 604/65

[56] References Cited

U.S. PATENT DOCUMENTS

| | | | |
|---|---|---|---|
| 3,816,035 | 6/1974 | Hutchisson | 210/477 |
| 3,960,466 | 6/1976 | Taylor | 417/234 |
| 4,083,777 | 4/1978 | Hutchisson | 210/646 |
| 4,210,138 | 7/1980 | Jess et al. | 604/67 |
| 4,229,299 | 10/1980 | Savitz et al. | 210/85 |
| 4,558,996 | 12/1985 | Becker | 417/374 |
| 4,599,055 | 7/1986 | Dykstra | 417/477 |
| 4,705,464 | 11/1987 | Arimond | 417/477 |
| 5,083,908 | 1/1992 | Gagnebin et al. | 417/477 |
| 5,250,027 | 10/1993 | Lewis et al. | 604/65 |
| 5,266,013 | 11/1993 | Aubert et al. | 417/474 |
| 5,460,493 | 10/1995 | Deniega et al. | 417/477.2 |
| 5,655,897 | 8/1997 | Neffel et al. | 417/477.2 |
| 5,752,813 | 5/1998 | Tyner et al. | 417/477.2 |

*Primary Examiner*—Teresa Walberg
*Assistant Examiner*—Leonid Fastovsky
*Attorney, Agent, or Firm*—R. William Beard, Jr.; Frohwitter

[57] ABSTRACT

The invention concerns a peristaltic pump comprising a rotor (109) provided with three turning rollers (110), means for driving the rotor, a support piece with a rounded portion arranged substantially concentric to the rotor and against which the rollers, when operating, come to compress a flexible pipe connected to a reservoir of liquid to push it outwards and means for turning said rotor by external means to air bleed the pipe. The rotor (109) is made of two concentric superposed parts the first (115) of which is coupled with drive means and the second (122, 123) bears the rollers. The rotor further comprises engaging-disengaging means (118, 120) whereby: when operating normally, its two parts co-operate for its rotation by its drive means; when it is rotated by external means, said parts are automatically disengaged. The invention is useful for subcutaneous or intravenous injection of medicinal solutions.

22 Claims, 6 Drawing Sheets

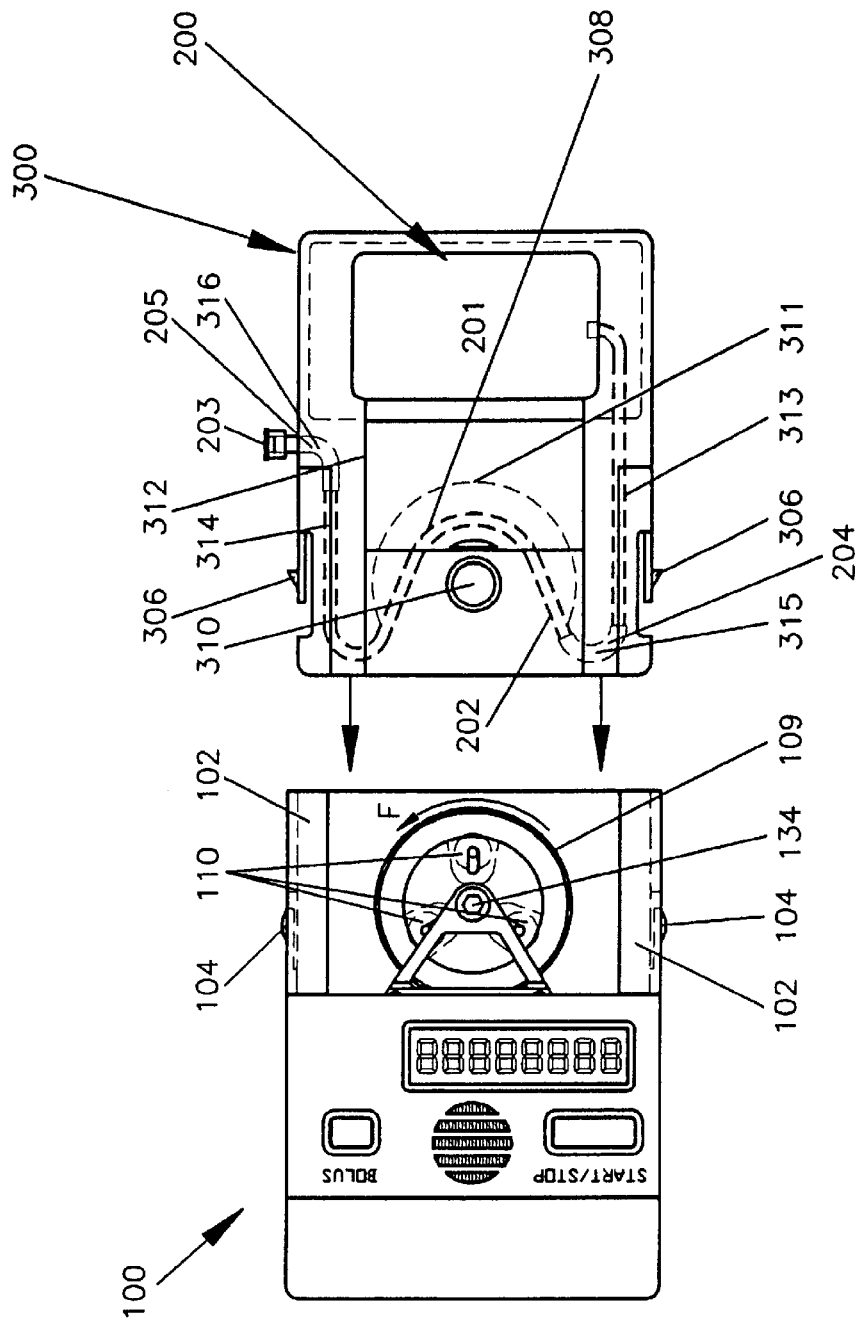

PORTABLE PERISTALTIC PUMP

This invention refers to portable peristaltic pumps. More specifically, it concerns a miniature peristaltic pump for the injection of drug solutions.

Miniature pumps or micropumps for medical use have been available for several years. Light and of small size, they can be worn discreetly and comfortably by the patient and permit the administration of controlled quantities of drug solutions to said patient, either subcutaneously or intravenously, continuously or according to a specific program, without his having to be confined to bed or hooked up to a cumbersome, costly and noisy machine.

Such pumps are most often of the rotary peristaltic type whose principle consists in having a flexible plastic tubing connected to a reservoir containing the solution and having it pressed locally against a rounded-off support piece by means of pressure rollers mounted on a rotor driven by a motor operating through a gear train. The liquid is thus drawn up from the reservoir and discharged toward the outlet to be injected into the patient.

Patents EP 388 787, EP 447 909, EP 521 184 and WO 94/06491 describe miniature peristaltic pumps of this type.

When designing such pumps, it is particularly important to be concerned about the problem presented by the discharging of the tubing, i.e. the discharge of any air it still contains, before inserting the needle into the patient. The rotor's rotation speed being very slow, generally less than 1 rpm, this operation must, in order not to take too much time, be done by making the rotor turn rapidly by external means. Patent EP 388 787 discloses a wheel which is part of the rotor and includes a series of holes into which one can put, for example, the point of a ballpoint pen to turn the wheel rapidly. That solution is certainly an interesting one, but no arrangement has been provided to keep this operation from damaging the gear train.

The document JP 58 070079 discloses, furthermore, a peristaltic pump provided with a disengaging system which enables the motor to be disengaged from the head of the pump. With the motor disengaged, the head of the pump may be turned more rapidly through a manual action.

However, it is to be noted that the disengagement is carried out by translating a control rod, which renders operation difficult.

Another major problem occurs during the design of a miniature peristaltic pump. The problem is that of the coupling between the rollers and the tubing being pressed by the rollers against the support piece.

Measurements have shown that the minimum pressure on a roller having a diameter of 5 mm, necessary to make a liquid flow in plastic tubing with an internal diameter of 1.47 mm and an external diameter of 1.96 mm is 95 grams. The corresponding tensile force exerted by the roller is 15 grams. The pressure on the roller may increase up to 150 grams without proportionally increasing the tensile force, which then only increases from 15 to 20 grams. However, beyond that limit, the tensile force increases very rapidly. In fact, it increases to 50 grams for a pressure of 200 grams, after which measurements become impossible.

Such observations are easily explained by the fact that once the tubing has been squeezed until it is completely sealed, any increase in pressure causes deformation of the plastic material and the corresponding tensile force then increases in relation to its elasticity module.

Thus, any variation in the position of the roller in relation to the tubing beyond that which achieves its closure, puts a heavy load on the roller-carrying rotor and its motor, which quickly causes jamming and therefore stopping of the pump. The effect is all the more pronounced in the miniature pumps that are obviously equipped with less powerful motors than the non-portable pumps.

Contrary to that, any variation in the position of the roller below the one that enables the complete closure of the tubing does not permit a normal flow of the liquid.

It is thus very important, in order to obtain a reliably functioning pump, that the distance separating the roller from the support piece be perfectly maintained and kept constant in order to avoid jamming or insufficient output.

Thus, if the support piece and the roller are fixed, extremely strict manufacturing tolerances are necessary and this therefore raises the cost price of the pump quite appreciably.

It is therefore preferable to accept lighter tolerances and to provide a means which automatically adjusts any gap in position between the support piece and the roller.

Patents EP 388 787 and EP 447 909, already referred to, succinctly describe arrangements to resolve this problem.

Patent EP 388 787 shows a support piece which has the shape of a hook articulated at one of its ends by a pin and presses against the tubing by means of a screw-compressed spring. This support piece, being almost always acted upon by two rollers, cannot ensure the correct adjustment of the position gaps for each of the separate rollers.

Patent EP 477 909 shows that the rollers are mounted on their axis with a slight radial play permitting them a certain radial clearance and that individual leaf springs acting directly on their central part push them towards the outside. Such an arrangement presents the double drawback of complicating the mounting of the rotor and to cause it to slide on the tubing rather than to turn. It is also shown in this document that the springs can be replaced by a unique elastic part, for which no description is supplied, and that they can be definitely omitted because the rollers are then radially displaced by the inherent elasticity of the tubing itself. This shows that the magnitude of the problem has not been fully understood.

The so-called cassette pumps are the most common in medical applications. They comprise two parts, on the one hand the actual pump with the motor, the drive electronics, the battery and the pump head formed by the rotor and the pressure rollers and, on the other, the cassette which clips onto the pump and includes the tubing and the support piece. The reservoir is either integrated into the cassette when it is of a small size, or arranged outside when the size is larger.

The pumps in Patents EP 447 909, EP 521 184 and WO 94/06491 are of this variety.

In these three cases, the cassette, which is assembled in a permanent manner, includes the tubing, the support piece and the reservoir. The pumps of the two EP patents are single-use-only because, once connected, the two units cannot be disconnected. At the end of treatment or when the cassette is empty, the entire unit is discarded, including the motor, the pump head, the support piece, the gear train and the circuit which are all still capable of functioning again. As far as the pump in the WO Patent is concerned, its cassette may be discarded at the same time as its reservoir. Thus, in these three pumps, components are being discarded which could still be used as they are because they are not worn out and have never been in contact with the medication injected into the patient.

Documents U.S. Pat. No. 4,817,057 and EP 120 284, moreover, describe peristaltic pumps with large size cassettes, i.e. non-portable ones. Even though the tubing can easily be inserted into, or removed from the cassette, it is fitted with a connecting nozzle to the tubing coming from the reservoir and its part that is subjected to the peristaltic action is specially designed to withstand the prolonged exposure to the compression effect of the rollers. Such a design has drawbacks because, not only does it not permit the re-use of the tubing to administer different drug solutions to different patients, but furthermore, the interconnecting operations of the two tubings increase the risk of bacterial contamination of the circuit.

The object of the invention is to provide a portable peristaltic pump that is free of the drawbacks of pumps known in the prior art.

The pump according to the invention includes:

a rotor equipped with at least one rotating roller, a means for driving said rotor, a means for controlling the said driving means, a support piece having a rounded-off part arranged in a substantially concentric manner to the said rotor and against which, during operation, said roller compresses a flexible tubing connected to a liquid reservoir to push the latter towards the exterior and a means to turn said rotor by an external action in order to affect discharge of the tubing.

This pump is mainly characterized by the fact that the rotor is arranged in two superimposed concentric parts of which one is connected to said driving means and of which the other carries said roller and by the fact that it furthermore includes a means for clutching/declutching due to which:

during normal operation, its two parts cooperate to enable its rotation through its driving means, when it is put into rotation by an external action, the parts are automatically disengaged.

Other characteristics of this invention are described in the specification to follow, which is based on the attached drawings and show, for explanatory but not restrictive purposes, a preferred design form of this pump. On these drawings:

FIG. 4 shows the manner in which the three units are connected;

FIG. 5 is a crosssection detail of FIG. 4 after connection has been made;

Figure 12:
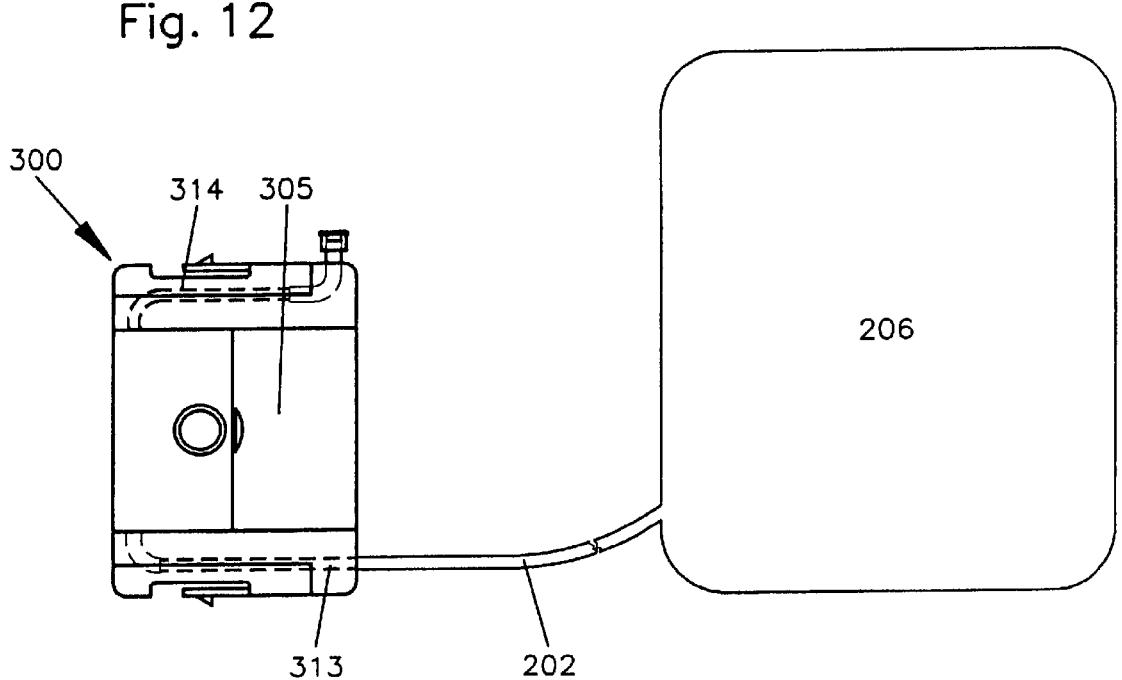

Finally, FIG. 12 illustrates an other embodiment of the reservoir unit.

As shown by FIGS. 1 through 5, the miniature pump according to the invention is composed of three units, a pump unit 100, a reservoir unit 200 and a cassette unit 300, which will also be called pump, reservoir and cassette respectively. Reservoir 200 fits in a manner that permits removal into cassette 300 which, in turn, connects in the same manner to pump 100.

To get an idea and simply as an example, the assembled pump is 110 mm long, 55 mm wide and 13 mm thick for a reservoir capacity of 10 ml.

Figure 1:
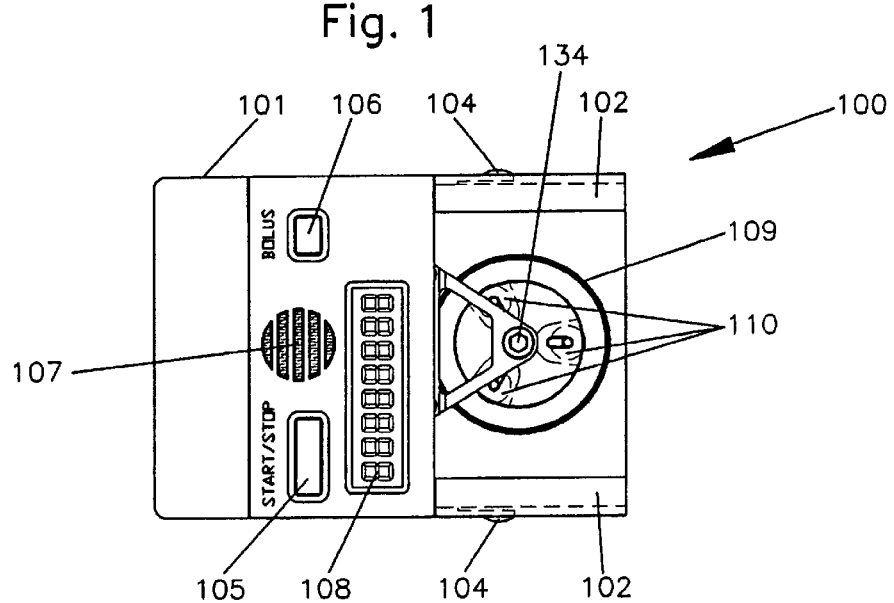
FIG. 1 is a general external view of the pump unit.

The pump unit 100, shown in FIG. 1, includes a rigid plastic case 101, the bottom of which extends on one side to form the base for two parallel sliders 102 that hold the cassette unit 300 like a drawer. As clearly shown in FIG. 5, each slider 102 is pierced by an opening 103 into which is fitted a flexible tongue 104 which forms a push button intended to release the cassette when it needs to be disconnected from the pump.

On its top surface, the case 101 has a 'START/STOP" button 105 which controls the starting and stopping of the pump, a 'BOLUS' button 106 which activates the administration of additional doses of solution, a sound alarm 107 and an LCD (liquid crystal display) 108.

Between its two sliders 102, case 101 shows a rotor 109 having three rollers 110, thus forming the pump head. A more detailed description of it will be given below, along with that of its driving means.

Figure 2:
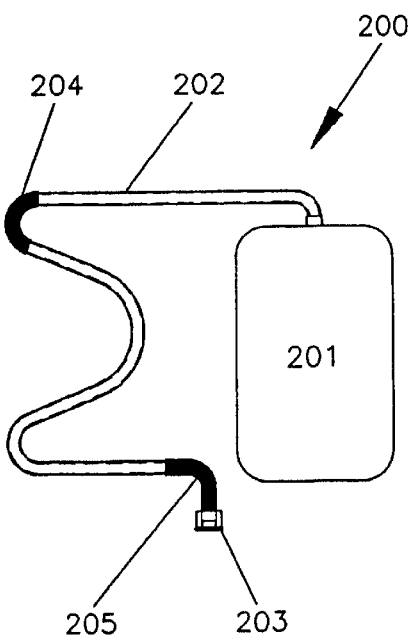
FIG. 2 represents the reservoir unit.

The reservoir unit 200, shown in FIG. 2, is formed by a plastic bag 201 having a volume of 10 ml in the embodiment shown and flexible plastic tubing 202 of which one end is connected to the bag and the other, intended for connection to a subcutaneous or intravenous injection needle, is sealed by a stopper 203. The tubing furthermore includes two rigid reinforced elbow-shaped connectors 204 and 205 that serve to clip it into the cassette 300, as will be more easily seen later on.

Figure 3:
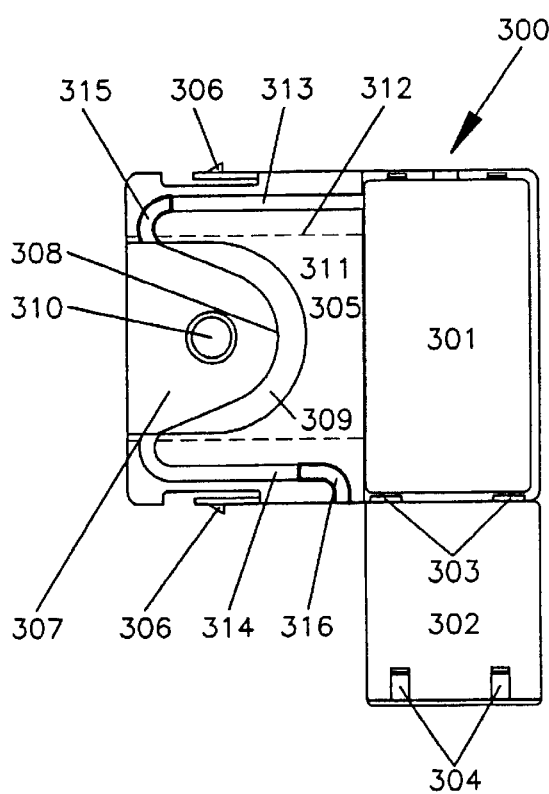
FIG. 3 represents the cassette unit.

The cassette unit 300, as seen from below in FIG. 3, is made of rigid plastic and includes a housing 301 intended to accommodate the plastic bag 201. It has more or less the same thickness and the same width as case 101 and has a cover 302 on the bottom, mounted on two hinges 303 and provided, at the other end, with tongues 304, which assure its closure by clipping. Housing 301 is extended by a plate 305 shaped and sized to fit, like a drawer, between the sliders 102 of the case. Two tongues 306, arranged on their sides, permit its clipping-in by the securing of their ends into openings 103, also shown in FIG. 5.

Plate 305 is perforated on the bottom side by a housing 307, of a general U shape, sized to accommodate the rotor 109 of the pump unit. To this end, it includes a central rounded-off part 308 of approximately 120 degrees, whose radius is slightly greater than that of the ring which covers the outside radius of rollers 110. It is on this rounded-off portion 308 that the three rollers successfully compress the flexible tubing 202 during operation. An additional rounded-off clearance 309 is provided around portion 308 to accommodate the lower part of rotor 109, of a larger diameter than the ring covered by the rollers, as will become apparent later on.

The bottom of housing 307 which forms the top surface of the unit is pierced at the center of the rounded-off portion 308 by a circular opening 310 which is the location where the shaft of rotor 109 fits in order to permit discharging the pump before use, as will be described later on. This opening can be closed off by a cover 311 sliding in a hollow space 312 of the upper wall of the unit.

Plate 305 also includes two channels 313 and 314, each arranged at the bottom of one of its sides parallel to the bottom. Channel 313 connects housing 301 to the front part of housing 307. Before it emerges in housing 307, it comprises an elbowed section 315, of a larger diameter, formed and sized in such a way as to fit and maintain the rigid connector 204 of flexible tubing 202 by clipping. Channel 314 begins at the front part of housing 307 at a location opposite from the location where the other channel arrives, and emerges outside after an elbowed section 316, which is of a larger diameter, and is formed and sized so as to accommodate and maintain the rigid connector 205 of tubing 202 by clipping.

Figure 6:
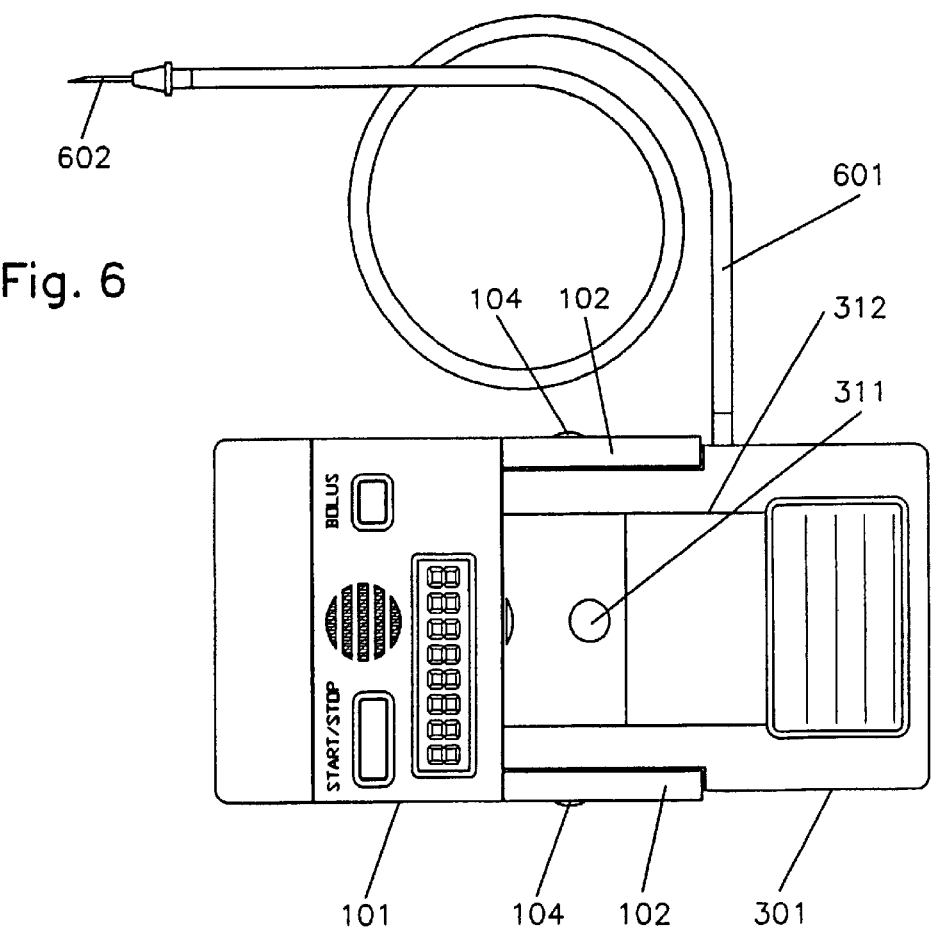
FIG. 6 is a general view of the assembled pump.
Figure 7:
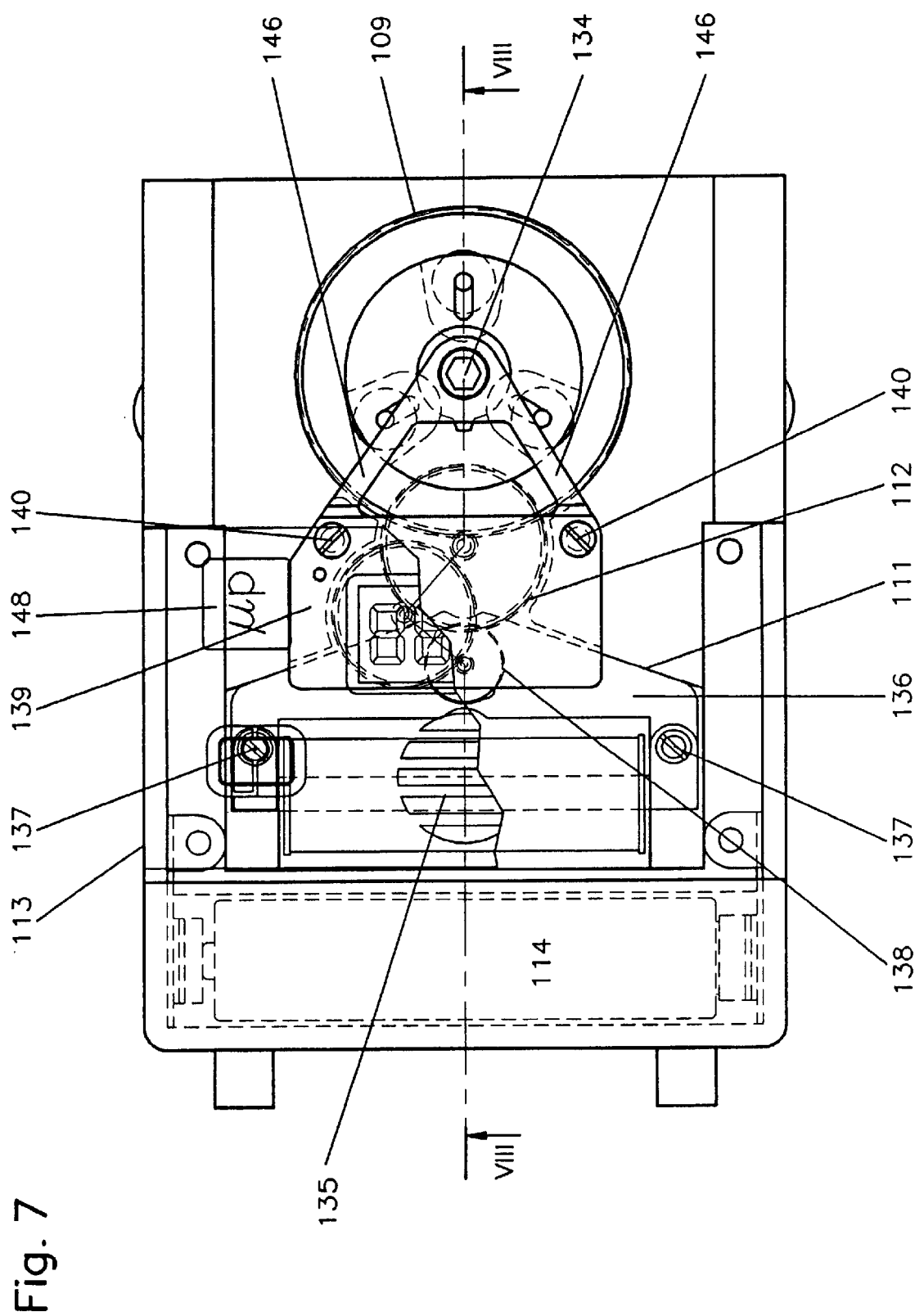
FIG. 7 is a top view of the pump unit.

We will now refer more specifically to FIGS. 4, 5 and 6, which show the manner in which the three units previously described connect to form the miniature pump according to the invention.

The reservoir unit 200 is placed first of all into the cassette unit 300. The plastic bag 201 is put into its housing 301 while the flexible tubing 202 is positioned in channels 313 and 314, ensuring that its two rigid connectors 204 and 205 are fitted into and clipped into elbowed sections 315 and 316 respectively of plate 305. After having closed cover 302, all that remains is the insertion of the cassette into the sliders 102 of pump unit 100 until the tongues 306 catch in the openings 103 (FIG. 5). The end of the lower part of rotor 109 occupies clearance 309 of plate 305 while the central section of flexible tubing 202 is automatically caught between rotor 109 and support piece 308. When the rotor is put into rotation in the direction of arrow F (counterclockwise), rollers 110 will alternately compress tubing 102 to push the solution that it contains to the outside.

The pump being loaded in this manner, stopper 203 of the tubing is removed and replaced as shown in FIG. 6 by tubing 601 which ends in a needle 602. Before inserting the latter into the patient, it is imperative to discharge the air still present in the circuit and to draw in the solution to be injected. As the normal rotation speed of rotor 109 is very slow (0.625 rpm), as will be described later on, this discharging operation must be done by rapidly turning the rotor by external means in order to not take too much time. The upper end of the shaft of the latter has, for this purpose, a shaped opening 134 appearing in opening 310 of the cassette and which permits, by means of an appropriate tool, the rapid rotation of the rotor until the droplets of solution to be injected come out of needle 602. The latter can then be inserted into the patient, after which the pump is started by pushing button 105 that controls the rotation of rotor 109 by mechanisms that will be described in detail below.

At the end of treatment, the uncoupling of pump unit 100 and cassette unit 300 takes place by pushing on the two buttons 104 so as to release tongues 306 of openings 103. The cassette can then be extracted by sliding it towards the outside before withdrawing thereof reservoir 200 which can be replaced by an other, the cassette and the pump being re-usable for another treatment.

Pump unit 100 will now be described referring to FIGS. 7 through 11 which show the rotor 109, a stepping motor 111, a gear train 112 connecting the motor to the rotor, an electronic control unit 113 and a small cylindrical battery 114.

Figure 8:
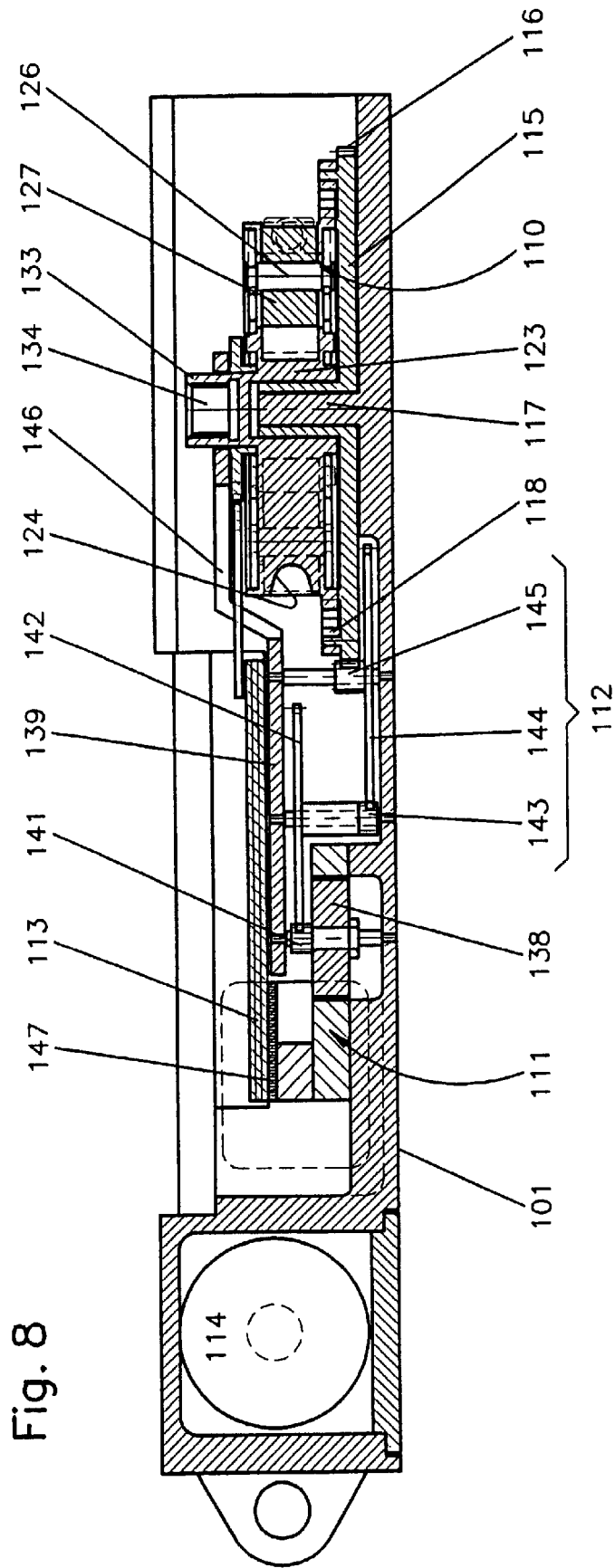
FIG. 8 is a cross section view of the pump unit according to line VIII-VIII of FIG. 7.
Figure 9:
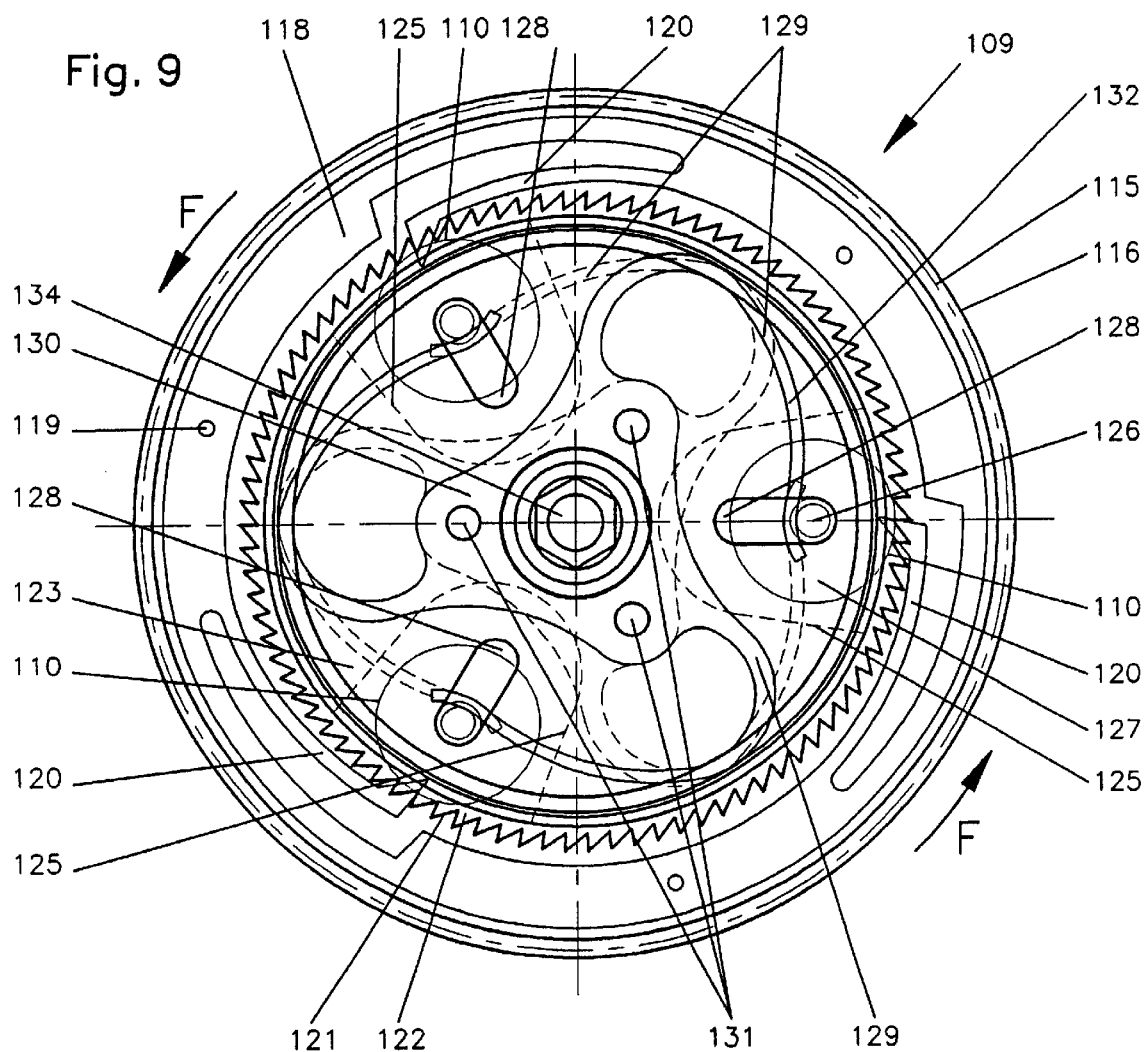
FIG. 9 is a top view of the rotor of the pump unit.

The rotor 109 shown in detail in FIGS. 8 and 9 includes a circular base 115 which has peripheral teeth 116 and is mounted freely rotating on a pivot 117 which is part of the bottom of case 101. A ring 118, of an external diameter which is slightly smaller than that of base 115, is mounted on the latter and affixed to it by screws 119. This ring has, towards the inside, three flexible arms 120 indented into its mass at 120 degrees one from the other and forming latches whose end interacts with the sawtooth periphery 121 of wheel 122. This latter constitutes the base of a cylindrical roller carrying plate 123 mounted on the axis of the base 115 around which it can turn freely.

The peripheral wall of plate 123 has a profile curved in towards the inside 124 in such a way as to form a channel for the flexible tubing 202. This same wall is also pierced by three housings 125 in the shape of a U, arranged at 120 degrees one from the other to accommodate the three pressure rollers 110 of the tubing.

Each roller 110 is formed by a shaft 126 and a cylindrical body 127 mounted on the shaft around which it can turn freely. The two ends of this shaft are fitted in oblong openings 128 arranged radially in the sections of the plate 123 which form the lower and upper flat walls of housing 125. The rollers are kept in a vertical position, i.e. with their axes parallel to the shaft of the rotor, and subjected to a radial force directed outward by means of two springs 129 arranged on each side of plate 123. Each spring includes a rigid central part 130, of a substantially triangular form, affixed to the plate concentrically to it by rivets 131 and three curved flexible spring arms 132 whose free ends rest on the respective ends of shafts 126 and push them outward in such a way that the rollers 110 exert a substantially constant force on tubing 202, which is set at 120 grams in the example described. The relative positioning errors of the rollers and the tubing, caused by inevitable manufacturing variations, are thus automatically compensated for, which avoids either excessive or insufficient compression of the tubing 202.

Plate 123 extends axially upward by a protrusion 133 traversing the central part 130 of the upper spring 129. This protrusion is pierced by the already mentioned shaped opening 134 into which fits, through the circular opening 310 of the cassette, the similarly shaped point of a tool (not shown) which permits the rapid rotation of the plate in order to discharge the pump.

Rotor 109 is put into rotation by the stepping motor 111 which is of the classic bipolar single-phase type and rotates at a speed of 16 rotations per second, at the rate of two steps per rotation. Its core coil and its stator, designated respectively by references 135 and 136, are affixed on feet formed in the base of case 101 by two screws 137. Its rotor 138 pivots between the base of the case and a bridge 139 affixed by screws 140 on feet that are part of the bottom of the case.

The rotor 138 carries a pinion 141 that meshes with a wheel 142 forming the first moving body of gear train 112. The pinion 143 of this wheel itself meshes with a wheel 144 whose pinion 145 finally meshes with the peripheral teeth 116 of the base 115 of rotor 109 in order to turn it at a speed of 0.625 rpm. Wheels 142 and 144 pivot, like rotor 138, between the bottom of the case and the link 139. The latter ends, after an elbow, in two arms 146, not shown in FIG. 9, whose common end includes a circular opening in which is held and in which pivots protrusion 133 of rotor 109.

During operation, when base 115 of the rotor is driven into the direction of arrow F by motor 111 through gear train 112, it turns with it ring 118 of which it is part. The three latches 120 of the latter then interact with the sawtooth periphery 121 of wheel 122 to put it into rotation, and along with it the roller-carrying plate 123 of which it forms the base. Thus, the rollers 110 compress tubing 102 one after the other to push the liquid that it contains into the direction of the injection needle 602.

When, to discharge the tubing, one causes the roller-carrying plate 123 to turn by means of an appropriately shaped tool introduced into opening 134, the base 115 and ring 118 become fixed, because they are restrained by the retention torque of motor 111 and its gear train 112. Disengagement then occurs automatically between ring 118 and wheel 122 due to the fact that the rotation of the latter causes the expulsion of the three latches 120 of sawtooth teeth 121. The roller-carrying plate 123 can thus be turned rapidly without any effect on the gear train or the motor.

Figure 10:
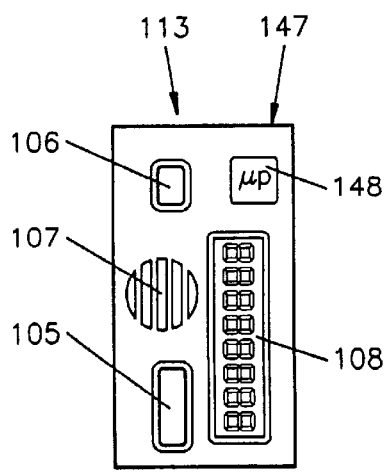
FIG. 10 shows the electronic control unit of the pump.

The electronic control unit 113, shown in FIG. 10, has as its base a printed circuit board 147, affixed under the upper face of the case and possessing buttons 105 and 106, the sound warning 107 and the LCD display 108. The board also has a microprocessor circuit 148 integrating the following main functions: voltage doubler, quartz time base, memory, LCD driver and sound generator. This microprocessor being of a known type, such as EPSON 62L35, will not be described in detail.

Figure 11:
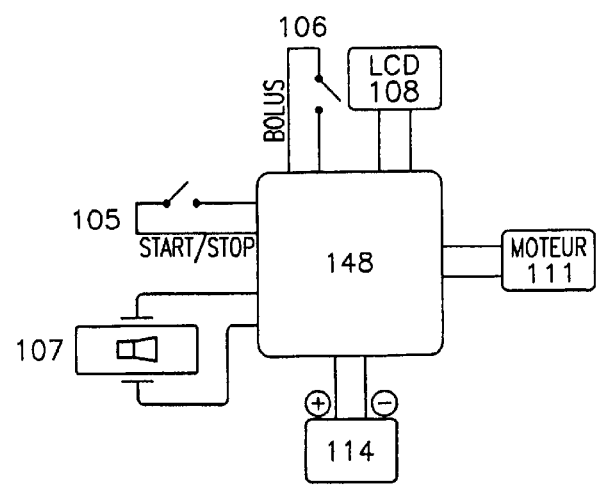
FIG. 11 is a diagram of the control circuit of the pump.

The whole of these components as well as battery 114 and the coil of motor 111 are interconnected according to the simplified diagram of FIG. 11. The microprocessor 148 is programmed according to methods well known by the expert to make the whole unit function as follows.

When switch 105 is activated for the first time, it triggers the operation of microprocessor 148 which, under the direction of a control program recorded in memory, applies drive impulses at a frequency of 32 Hz to the terminal of the stepping motor 111, triggering its rotation at a speed of 16 rpm. The roller-carrying rotor 109 is then driven at a speed of 0.625 rpm. The operation of the pump is interrupted when switch 105 is activated a second time.

For example, with a rotation radius of the roller-carrying plate of 10.44 mm and a speed of 0.625 rpm, the solution flows through the tubing at a speed of 41 mm/min. By choosing tubing with a 1.47 mm internal diameter, the instantaneous output of the pump is thus 69.54 $mm^3$/minute, or 100 $cm^3$ per day.

The microprocessor 148 also permits, in response to pushing button 106, the bypassing of the control program put into memory, to permit the injection of a specific additional quantity of solution (bolus). This procedure is specifically intended for pain-relief treatment.

The pump is also equipped with mechanisms permitting the activation of the audible warning 107 and/or LCD display 108 in case of malfunction: failure to respect the program, stoppage, obstruction of needle, depletion of battery . . . Since these mechanisms are not the subject of this patent, they will not be described.

We will finally refer to FIG. 12, which shows a design variation of cassette unit 300 for treatments requiring injection of large amounts of solution. The cassette can certainly be extended to accommodate a larger reservoir, but if the volume of the latter exceeds 20 ml, the overall dimensions of the pump risk making it impractical. For this reason, the cassette unit of FIG. 12 contains only plate 305 described in FIG. 3, the same references being used to designate the same elements. The reservoir unit then includes a large volume bag 206 which is not fitted into the cassette but merely connected to it by longer flexible tubing 202 identical to that described in FIG. 2.

What is claimed is:

1. A portable peristaltic pump comprising:
   a rotor (109) equipped with at least one turning roller (110),
   a means for driving (111, 112) said rotor,
   a means for controlling (113) said driving means,
   a support piece equipped with a rounded-off part (308) arranged in a substantially concentric manner to the rotor, wherein during operation said at least one turning roller compresses a flexible tubing (202) against the rounded-off part (308), wherein said flexible tubing (202) is connected to a liquid reservoir (210), and
   a means for turning said rotor by an external action to affect discharge from the tubing, wherein the rotor comprises two concentric superimposed parts and an engaging-disengaging means, wherein the first part is connected to said means for driving and the second part carries said at least one turning roller;
   wherein the engaging-disengaging means engages the first and second parts, during normal operation, to enable rotation of the second part by the means for driving,
   wherein the engaging-disengaging means automatically disengages the first and second parts when the second part of said rotor is put into rotation through the means for turning by external action.

2. A portable peristaltic pump according to claim 1, wherein the first part of the rotor includes a toothed wheel (115) which cooperates with said means for driving wherein the second part of the rotor includes a toothed wheel (122) which forms a base of a roller-bearing plate (123), and that said engaging-disengaging means comprises a ring (118) affixed to the toothed wheel (115) of the first part and concentrically to it, surrounding the toothed wheel (122) of the second part and having, towards the inside, at least one flexible arm (120) forming a latch and whose end cooperates with the toothed wheel of the second part.

3. A portable peristaltic pump according to claim 1, wherein the means for turning the rotor by an external action includes a protrusion (133) which extends from a shaft of the rotor and is pierced by an shaped opening (134) intended to accommodate a tool of corresponding shape.

4. A portable peristaltic pump according to claim 1, wherein:
   the rotor and and the at least one turning roller, said means for driving and said means for controlling form a first unit (100), called the pump unit,
   the support piece is part of a second unit (300), called the cassette unit,
   said units are each equipped with means permitting their connection and
   the cassette unit includes means (313, 314) to interchangeably accommodate said tubing which is an integral part of the reservoir and to automatically position the tubing so that it fits against said rounded-off section at the moment of connection of the two units, to be compressed there by said at least one turning roller, the tubing and the reservoir thus forming a third unit (200) called the reservoir unit, which can easily be exchanged after use.

5. A portable peristaltic pump according to claim 4, wherein the cassette unit includes a plate (305) which fits, like a drawer, into the pump unit and is pierced by a housing (307) of a U shape, shaped and proportioned so as to surround the rotor and whose rounded-off base (308) constitutes the support piece of the tubing and that the means for accommodating and positioning said tubing include a first (313) and a second (314) channel arranged along the respective sides of said plate, said channels having one end opened toward the outside of the plate and their other ends emerging opposite one another in the entrance of said housing.

6. A portable peristaltic pump according to claim 5, wherein said channels include a means for holding said tubing by clipping it in.

7. A portable peristaltic pump according to claim 6, wherein said means for holding the tubing is constituted of elbowed sections (315, 316) of said channels, shaped and sized so that sections (205, 205) of corresponding shape of said tubing fit into and are held there by clipping-in.

8. A portable peristaltic pump according to claim 4, wherein the cassette unit is affixed into the pump unit by clipping its plate into sliders (102) of said pump unit.

9. A portable peristaltic pump according to claim 4, wherein the cassette unit includes a housing (301) to hold the liquid reservoir.

10. A portable peristaltic pump according to claim 1, wherein the rotor includes means for automatic adjustment of position gaps between the at least one turning roller and the support piece.

11. A portable peristaltic pump according to claim 10, wherein the at least one turning roller (110) includes a substantially cylindrical unit (127) and a shaft (126) on which said unit is rotatable mounted, wherein the ends of said shaft are fitted in oblong openings (128) arranged radially in the rotor and that said compensating means include two springs (129) arranged at the level of the respective ends of the shaft of the roller, each including a central part (130) concentric to the rotor and a curved spring arm (132) of which one end is part of said central part and whose other end is fitted against the corresponding end of the shaft of the roller to push it radially towards the outside thus permitting said roller to exert a substantially constant compression force on the tubing.

12. A portable peristaltic pump comprising:

a rotor (109) equipped with at least one turning roller (110), a driver (111, 112) of said rotor, a controller (113) of said driver, a support piece equipped with a rounded-off part (308) arranged in a substantially concentric manner to the rotor, wherein said at least one turning roller compresses a flexible tubing (202) against the rounded-off part (308), wherein said flexible tubing (202) is connected to a liquid reservoir (210), and a turner of said rotor by an external action to affect discharge from the tubing, wherein the rotor comprises two concentric superimposed parts and a clutch, wherein the first part is connected to said driver and the second part carries said at least one turning roller;

wherein the clutch engages the first and second parts, during normal operation, to rotate the second part by the driver, wherein the clutch automatically disengages the first and second parts when the second part of said rotor is turned by said turner by an external action.

13. A portable peristaltic pump according to claim 12, wherein the first part of the rotor has a first toothed wheel (115) which cooperates with said driver, wherein the second part of the rotor has a second toothed wheel (122) which forms a base of a roller-bearing plate (123), and that said clutch comprises a ring (118) affixed concentrically to the first toothed wheel (115) of the first part and surrounding the second toothed wheel (122) of the second part, wherein the clutch has at least one flexible arm (120), the distal end of which latches with the second toothed wheel of the second part.

14. A portable peristaltic pump according to claim 12, wherein the turner of the rotor by an external action comprises a protrusion (133) which extends from a shaft of the rotor, wherein the protrusion has a shaped opening (134) for engaging a tool.

15. A portable peristaltic pump according to claim 12, wherein the rotor with the at least one turning roller, said driver and said controller comprise a pump unit (100), wherein the support piece is part of a cassette unit (300), wherein said units are connectable with each other, wherein the cassette unit comprises a positioner of said tubing so that it fits against said rounded-off section when the pump and cassette units are connected to be compressed by said at least one turning roller, wherein the tubing and the reservoir comprise a reservoir unit (200) which is replaceable after use.

16. A portable peristaltic pump according to claim 15, wherein the cassette unit includes a plate (305) which fits into the pump unit and is pierced by a housing (307) of a U shape, wherein the housing is shaped and proportioned so as to surround the rotor and whose rounded-off base (308) constitutes the support piece of the tubing and wherein the positioner of said tubing has a first (313) and a second (314) channel arranged along the respective sides of said plate, said channels having one end opened toward the outside of the plate and their other ends emerging opposite one another in the entrance of said housing.

17. A portable peristaltic pump according to claim 16, wherein said channels comprise holders of said tubing, wherein the tubing is clipped into the holders.

18. A portable peristaltic pump according to claim 17, wherein said holders of the tubing comprise elbowed sections (315, 316) in said channels and wherein said tubing comprises connectors (204, 205), wherein the connectors and elbowed sections are shaped and sized so that the connectors fit and clip into said elbowed sections.

19. A portable peristaltic pump according to claim 15, wherein the cassette unit is affixed into the pump unit by clipping a plate of the cassette unit into sliders (102) of said pump unit.

20. A portable peristaltic pump according to claim 15, wherein the cassette unit comprises a housing (301) to hold the liquid reservoir.

21. A portable peristaltic pump according to claim 12, wherein the rotor comprises an adjuster of a gap between the at least one turning roller and the support piece.

22. A portable peristaltic pump according to claim 21, wherein the at least one turning roller (110) comprises a substantially cylindrical unit (127) and a shaft (126), wherein the cylindrical unit is rotatably mounted on the shaft, wherein the ends of said shaft fit in oblong openings (128) arranged radially in the rotor, wherein the adjuster of the gap comprises two springs (129) arranged at the level of the respective ends of the shaft of the roller, each including a central part (130) concentric to the rotor and a curved spring arm (132) of which one end is part of said central part and whose other end fits against the corresponding end of the shaft of the roller to push it radially towards the outside so that said roller exerts a substantially constant compression force on the tubing.

* * * * *